United States Patent [19]

Müller et al.

[11] 4,447,623
[45] May 8, 1984

[54] PROCESS FOR THE PREPARATION OF 4,5-DICHLORO-1,2-DITHIACYCLOPENTEN-3-ONE

[75] Inventors: Rolf Müller, Karben; Herbert Wille, Frankfurt am Main, both of Fed. Rep. of Germany

[73] Assignee: Cassella Aktiengesellschaft, Frankfurt am Main, Fed. Rep. of Germany

[21] Appl. No.: 422,843

[22] Filed: Sep. 24, 1982

[30] Foreign Application Priority Data

Jan. 21, 1982 [DE] Fed. Rep. of Germany ....... 3201761

[51] Int. Cl.³ .......................................... C07D 339/04
[52] U.S. Cl. .................................................. 549/36
[58] Field of Search ........................................ 549/36

[56] References Cited

U.S. PATENT DOCUMENTS 3,062,833  11/1962  Boberg et al. .......................... 549/36

FOREIGN PATENT DOCUMENTS 1101174  3/1961  Fed. Rep. of Germany .
1128432  4/1962  Fed. Rep. of Germany .

Primary Examiner—Norma S. Milestone
Attorney, Agent, or Firm—Connolly and Hutz

[57] ABSTRACT

An improved process for preparation of 4,5-dichloro-1,2-dithia-cyclopenten-3-one of the formula

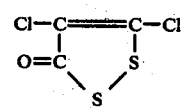

by reacting hexachloroprene with sulphur at elevated temperatures, wherein the improvement comprises hydrolyzing by-product sulphur chlorides by conducting the reaction in the presence of water.

9 Claims, No Drawings

PROCESS FOR THE PREPARATION OF 4,5-DICHLORO-1,2-DITHIACYCLOPENTEN-3-ONE

The invention relates to a process for the preparation of 4,5-dichloro-1,2-dithiacyclopenten-3-one, also known as 5-oxo-3,4-dichloro-1,2-dithiol of the formula I

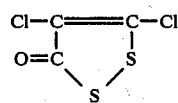   (I)

which process can also be carried out on an industrial scale.

4,5-Dichloro-1,2-dithia-cyclopenten-3-one is employed, for example, for combating slime fungus in the paper industry, compare German Patent Specification No. 2,913,593. Two processes are known for preparing the compound of the formula I, namely, 1, the reaction of hexachloropropene with sulphur or sulphur chlorides in the presence of a Friedel-Crafts catalyst (German Patent Specification No. 1,102,174 corresponding to U.S. Pat. No. 3,062,833, and Friedrich Boberg: Ann. Chem. 679 (1964), 109 to 118) and, 2, the reaction of hexachloropropene with sulphur at temperatures above 160° C. (German Patent Specification No. 1,128,432 and Friedrich Boberg loc. cit.). In the process mentioned first, the reaction between hexachloropropene, sulphur and aluminium chloride sets in very violently within a narrow temperature range, at about 46° C., so that, in the case of fairly large batches, it is no longer possible to remove the quantity of heat formed. Furthermore, the reaction mixture solidifies completely a short time after the reaction has set in, and the stirrer comes to a standstill. Not even a large excess of hexachloropropene can remove this drawback. Customary solvents, such as dichlorobenzene or nitrobenzene, are attacked. In addition, there is always a little hexachloroethane formed, which cannot be removed in the case of batches on an industrial scale because it sublimes readily. For these reasons, technical production free from problems is not possible by the process first mentioned.

In both processes the desired end product is obtained by hydrolysis of the intermediate products which are first formed. In the process first mentioned this is the 3,4,5-trichloro-1,2-dithiolium-AlCl₄ adduct and in the second process it is 3,4,5-trichloro-1,2-dithiolium chloride. In the second process, the crystalline intermediate product is filtered off with suction and is washed with benzene and then with carbon disulphide in order to remove chlorides of sulphur which are formed and which adhere to it. On an industrial scale, this involves difficulties, so that this process also is not suitable for the preparation of the compound of the formula I on an industrial scale. If the chlorides of sulphur are not completely removed before the 3,4,5-trichloro-1,2-dithiolium chloride is hydrolysed, rubber-like products are formed in the hydrolysis which make subsequent distillation of the 4,5-dichloro-1,2-dithiacyclopenten-3-one impossible. In both the known processes, fairly large quantities of chlorides of sulphur, in particular sulphur dichloride and disulphur dichloride, are formed, which raises considerable problems on the score of industrial safety. Additional difficulties also arise in the subsequent destruction of the chlorides of sulphur. However, according to Friedrich Boberg, loc. cit., page 110, the presence of disulphur dichloride is a significant factor in the reaction between hexachloropropene and sulphur, since a poorer yield is obtained by distilling off the $S_2Cl_2$ during the reaction.

It has now been found, surprisingly, that 4,5-dichloro-1,2-dithiacyclopenten-3-one can be prepared, even on an industrial scale, if the chlorides of sulphur formed in the reaction between hexachloropropene and sulphur are hydrolysed by the addition of water at the rate at which they are formed. The invention relates, therefore, to a process for the preparation of 4,5-dichloro-1,2-dithiacyclopenten-3-one by reacting hexachloropropene with sulphur at elevated temperatures, which is characterised in that water is added during the reaction. It is advantageous to add the water continuously during the whole reaction time. The water can be added in liquid or vapour form. The reaction temperature can be varied, for example from 150° C. up to the boiling point of hexachloropropene (210° C.). However, for reasons relating to the reaction rate, it is advantageous to keep it between 155° C. and 185° C., preferably between 157° and 175° C.; the reaction is more easily carried out if the temperature is controlled relatively precisely. The molar ratio between hexachloropropene, sulphur and water can be varied within wide limits, since the unreacted hexachloropropene is recovered. It is advantageous to add as much water in each stage of the reaction as is required for the hydrolysis of the primary reaction products formed, of which the chlorides of sulphur can be recognised readily in the reflux by means of their yellow colour. Normally, relative to hexachloropropene actually reacted, the hexachloropropene:sulphur:water molar ratio is 1:(2.5 to 3.0):(2.0 to 2.5). It is not necessary to use more water or more sulphur. If more sulphur is employed, sulphur remains in the distillation residue, which is undesirable for ecological reasons. On the other hand, it is advantageous to employ hexachloropropene in excess, in which connection an excess of 5 to 25% by weight is sufficient as a rule, so that the resulting molar ratio for the reactants to be employed is hexachloropropene:sulphur:water=1:(2 to 2.9):(1.6 to 2.4). If the quantity of water added is correctly adjusted, no more chlorides of sulphur are present in the reaction mixture at the end of the reaction. It may be assumed that 3,4,5-trichloro-1,2-dithiolium chloride II

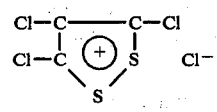   (II)

and chlorides of sulphur, in particular $S_2Cl_2$, are formed as intermediates in the reaction between hexachloropropene and sulphur in the process according to the invention and that the products formed as intermediates are immediately hydrolysed at the high reaction temperatures by the water present, whereby 4,5-dichloro-1,2-dithiacyclopenten-3-one (I) is formed from the 3,4,5-trichloro-1,2-dithiolium chloride (II), and sulphur, sulphur dioxide and hydrogen chloride are formed from the chlorides of sulphur, and that the sulphur thus formed enters again into the reaction. Accordingly, the following overall equation is an approximate representation of the course of the reaction for the whole reaction:

$Cl_3C-CCl=CCl_2 + 2.5S + 2H_2O \rightarrow I + \tfrac{1}{2}SO_2 + 4HCl$

Since the water is added in an amount such that the 3,4,5-trichloro-1,2-dithiolium chloride and the chlorides of sulphur formed are rapidly hydrolysed, the stationary concentrations of chlorides of sulphur and 3,4,5-trichloro-1,2-dithiolium chloride and of water present during the reaction by the process according to the invention are low; only the stable products hexachloropropene, sulphur and 4,5-dichloro-1,2-dithiacyclopenten-3-one are present in large quantities. The gases formed in the hydrolysis of the chlorides of sulphur, HCl and $SO_2$, can be absorbed in water without any problem. Because of the small quantities of chlorides of sulphur present in the reaction mixture, special industrial safety precautions are not required. The duration of the reaction depends, above all, on the reaction temperature chosen and on the quantity of water and heat supplied to the reaction mixture, and is generally 6 to 60 hours. As a rule, the reaction mixture is worked up by distillation, but working up can also be effected by crystallisation, for example from petroleum ether. Hexachloropropene which may have been employed in excess is recovered as first runnings by distilling the reaction mixture, and can be re-used without further purification. 4,5-Dichloro-1,2-dithiacyclopenten-3-one is obtained in a yield of approx. 90% of theory and in a purity, determined by gas chromatography, of over 99% by the process according to the invention.

EXAMPLE 1

84.6 kg (340 mols) of hexachloropropene and 27.2 kg (850 mols) of sulphur are heated to an internal temperature of 165° C. in a 125 l enamelled kettle equipped with oil heating. 12 kg (667 mols) of steam are then blown in through the bottom valve in the course of about 8 hours. The internal temperature remains between 165° C. and 172° C., and the two-phase mixture of hexachloropropene and water can be seen all the time in the reflux condenser, the hexachloropropene being coloured yellow by sulphur chloride. When, after about 8 hours, the 12 kg of steam have been added, the yellow colour of the sulphur chloride disappears in the reflux, and the reaction is complete. The mixture is cooled to 80° to 100° C., steam is passed in again for a short period and the mixture is then distilled in vacuo at 16 mbar. This gives 5.3 kg (21.31 mols) of hexachloropropene boiling at 80° to 90° C./16 mbar and 54.1 kg of 4,5-dichloro-1,2-dithiacyclopenten-3-one of a purity, determined by gas chromatography, of 99%. Yield: 90,8% of theory, relative to hexachloropropene which has reacted.

EXAMPLE 2

1,600 g (50 mols) of sulphur and 5,480 g (22 mols) of hexachloropropene are initially taken in a 6 l four-necked flask equipped with a stirrer, a thermometer, a glass inlet tube and a reflux condenser, and the mixture is warmed in an oil bath at 170° C., while stirring. When the internal temperature has reached 155° C., steam is passed in. The rate of addition is adjusted so that the internal temperature remains at 155° to 160° C. After about 45 hours, 720 g (40 mols) of steam have been introduced and the reaction is complete. Working up as described in Example 1 gives a yield of 810 g of recovered hexachloropropene and 3,247 g of 4,5-dichloro-1,2-dithiacyclopenten-3-one of purity, determined by gas chromatography, of 99%. Yield: 92,6% of theory, relative to hexachloropropene which has reacted.

EXAMPLE 3

The procedure followed is as described in Example 2, but the quantity of water indicated is added dropwise in the course of the time indicated, in the form of liquid by means of a metering funnel equipped with a glass valve. The product is obtained in similar purity and yield.

EXAMPLE 4

The procedure followed is as described in Example 1 until the working-up is begun. The small excess of water is then removed by vacuum distillation and the contents of the flask are cooled to about 60° C. and then recrystallised from petroleum ether. The product is obtained in a yield of about 88% of theory and in a purity, determined by gas chromatography, of over 99.5% The unreacted hexachloropropene is recovered by distilling the mother liquor.

What is claimed is:

1. In the process for preparation of 4,5-dichloro-1,2-dithiacyclopenten-3-one by reacting hexachloropropene with sulphur at elevated temperatures, the improvement comprises simultaneously hydrolyzing by-product sulphur chlorides by conducting the reaction in the presence of water at a temperature of about 150° to 210° C.

2. The process according to claim 1 wherein water is added to the reaction continuously.

3. The process according to claim 1 wherein water is added during the entire reaction time.

4. The process according to claim 1 wherein water is added to the reaction in the form of steam.

5. The process according to claim 1 wherein water is added to the reaction mixture at a temperature of 155° to 185° C.

6. The process according to claim 6 wherein water is added to the reaction mixture at a temperature of 157° to 175° C.

7. The process according to claim 1 wherein only as much water is added to the reaction as is required to hydrolyse the reaction products formed and water is added at the rate reaction products form.

8. The process according to claim 1 wherein 1.6 to 2.4 moles of water per mole of hexachloropropene are added to the reaction.

9. The process according to claim 1 wherein the molar ratio of hexachloropropene:sulphur:water is 1:(2.5 to 3.0):(2.0 to 2.5).

* * * * *